(12) United States Patent
Stratis-Cullum et al.

(10) Patent No.: US 9,605,034 B2
(45) Date of Patent: Mar. 28, 2017

(54) METHOD AND USE FOR SURFACE DISPLAY OF PROTEINS AND PEPTIDE DERIVATIVES IN A BACTERIAL THERMOPHILE (71) Applicant: THE UNITED STATES OF AMERICA AS REPRESENTED BY THE SECRETARY OF THE ARMY, Washington, DC (US)

(72) Inventors: Dimitra Nikolaos Stratis-Cullum, Laurel, MD (US); Bryn Lauren Adams, Silver Spring, MD (US); Margaret Mary Hurley, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/838,392

(22) Filed: Aug. 28, 2015

(65) Prior Publication Data
US 2017/0058004 A1    Mar. 2, 2017

(51) Int. Cl.
C07K 14/195    (2006.01)
C12N 15/70    (2006.01)
C12N 15/74    (2006.01)

(52) U.S. Cl.
CPC .......... C07K 14/195 (2013.01); C12N 15/70 (2013.01); C12N 15/74 (2013.01); C07K 2319/02 (2013.01); C07K 2319/21 (2013.01); C07K 2319/50 (2013.01)

(58) Field of Classification Search
None
See application file for complete search history.

(56) References Cited

U.S. PATENT DOCUMENTS 5,348,867 A    9/1994   Georgiou et al.

OTHER PUBLICATIONS

Brosig et al., "Crystal Structure of a Major Outer Membrane Protein from Thermus thermophilus HB27", JMB, 2009, 385:1445-1455. doi:10.1016/j.jmb.2008.12.003.*

* cited by examiner

Primary Examiner — Suzanne M Noakes
(74) Attorney, Agent, or Firm — Christos S. Kyriakou; Robert Thompson (57) ABSTRACT Provided are compositions are methods for discovery of new materials and interactions under extreme environmental conditions such as elevated temperatures at or in excess of 60° C. A synthetic thermostable protein is provided that is linked to a target peptide. A library of target peptides may be linked to a plurality of the thermostable proteins for expression on the cell surface of a thermophilic organism. The composition employs a modified form of the *T. thermophilus* TtoA protein that has a non-naturally occurring N-terminus for associating with a target peptide thereby expressing the target peptide on the outer cell membrane where the thermophilic protein is stable at high temperatures for discovery of materials useful in extreme environments or for us in study conditions that require or suffer under elevated temperatures.

9 Claims, 6 Drawing Sheets

METHOD AND USE FOR SURFACE DISPLAY OF PROTEINS AND PEPTIDE DERIVATIVES IN A BACTERIAL THERMOPHILE

GOVERNMENT INTEREST

The invention described herein may be manufactured, used, and licensed by or for the United States Government.

FIELD OF USE

In embodiments the invention relates to the expression of proteins. More particularly, the invention relates to the expression of proteins on a cell for use in extreme temperature conditions. Provided are expression systems in a thermophile that are fully capable of function at extreme temperatures.

BACKGROUND

Proteins and peptide derivatives can currently be displayed on the surface of bacteria, viruses, and yeast for a variety of biotechnological applications such as biopharmaceutical development, peptide discovery, and basic research. Phage display remains the most widely used method for expressing protein libraries. Bacteriophage (phage) display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409; 5,403,484; 5,571,689; 5,663,143.

More recently, eukaryotic and prokaryotic expression systems have been considered for peptide display. Most investigations have focused on eukaryotic yeast for display of protein libraries, but similar systems are also being developed using prokaryotic hosts with E. coli being the primary expression host studied. Cell surface display is attractive since fluorescence activated cell sorting (FACS) can be applied for sensitive, quantitative library analysis and screening. Furthermore, cell display enables simple clonal and library manipulation and propagation and direct measurement of the relative binding constants of isolated clones. However, the general utility of bacterial display for screening peptide and protein libraries is currently limited by the suitability of typical display scaffolds—including outer membrane proteins, fimbria (FimH), and flagella (FLITRX). While such systems have had some success in antibody and protein epitope mapping experiments, less success has been achieved in the isolation of soluble affinity reagents, which typically requires grafting of the peptides into constrained, soluble scaffold proteins. Given these problems, bacterial display systems have not proven generally useful for generating affinity reagents.

In addition to the above problems with prior cell display systems, each suffers from usefulness in limited temperature ranges that are amenable to host cell viability (typically 20-40° C.). As such, new methods and compositions are required for peptide and protein display.

SUMMARY

The following summary is provided to facilitate an understanding of some of the innovative features unique to the present invention and is not intended to be a full description. A full appreciation of the various aspects of the invention can be gained by taking the entire specification, claims, drawings, and abstract as a whole.

Provided are synthetic peptides and proteins that serve for the display of a target peptide on the extracellular surface of a cell. A thermostable protein according to the invention includes a first peptide comprising a C-terminal sequence of a TtoA protein or conservative analog thereof and a second peptide comprising a N-terminal sequence of said TtoA protein or conservative analog thereof, said first peptide bound to said second peptide by an intermediate linker domain linking a C-terminus of said first peptide and a N-terminus of said second peptide. The term "thermostable" as used herein represents a protein or peptide capable of maintaining structure at temperatures in excess of 50° C., and in some aspects at temperatures of 60° C. to 98° C. In some aspects, the first peptide includes residues 64-214 of SEQ ID NO: 1, or a conservative analog thereof. In some aspects, the second peptide includes residues 11-63 of SEQ ID NO: 1, or a conservative analog thereof. Optionally, a thermostable protein includes a signal peptide associated with a N-terminus of the first peptide. Optionally, a thermostable protein includes a binding peptide associated with a C-terminus of the second peptide, optionally a P2X peptide. The linker in the thermostable protein optionally includes an amino acid, optionally 20-40 amino acids. In some aspects, a thermostable protein includes or consists of the sequence of SEQ ID NO: 2 or a conservative analog thereof.

Also provided according to some aspects is a nucleic acid sequence encoding the thermostable protein. Optionally, a nucleic acid sequence includes SEQ ID NO: 4.

Also provided are processes of expressing a target on a cell surface including: providing an expression vector encoding a thermostable protein that includes a first peptide comprising a C-terminal sequence of a TtoA protein or conservative analog thereof; a second peptide comprising a N-terminal sequence of said TtoA protein or conservative analog thereof, said first peptide bound to said second peptide by an intermediate linker domain linking a C-terminus of said first peptide and a N-terminus of said second peptide; and a library member; transfecting a cell with the vector; and incubating said cell under conditions suitable for expression of a protein from said vector, thereby expressing said thermostable protein on the surface of said cell. A process optionally further includes generating the vector, the step of generating including amplifying a nucleic acid sequence encoding said peptide absent said library member using a forward primer or reverse primer encoding said library member to produce an expression construct; and ligating said expression construct to a vector to form said expression vector. In some aspects, the first peptide includes residues 64-214 of SEQ ID NO: 1, or a conservative analog thereof. In some aspects, the second peptide includes residues 11-63 of SEQ ID NO: 1, or a conservative analog thereof. Optionally, a thermostable protein includes a signal peptide associated with a N-terminus of the first peptide. Optionally, a thermostable protein includes a binding peptide associated with a C-terminus of the second peptide, optionally a P2X peptide. The linker in the thermostable protein optionally includes an amino acid, optionally 20-40 amino acids. In some aspects, a thermostable protein includes or consists of the sequence of SEQ ID NO: 2 or a conservative analog thereof.

DETAILED DESCRIPTION

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions are described as using specific materials in a particular order, it is appreciated that the described materials or order may be interchangeable such that the description of the invention includes multiple parts or steps arranged in many ways as is readily appreciated by one of skill in the art.

Provided are new compositions and methods useful for display of proteins and peptides of unknown or known sequence, functional characteristics, biological characteristics, or chemical characteristics such as from peptide libraries. The compositions and methods employ a novel, non-biologically available protein capable of expression on a cell surface, optionally on the surface of a thermophilic organism. As such, a composition includes a synthetic thermostable unconstrained display (STUD) protein. STUD is a novel, synthetic protein that does not naturally exist in any organism is custom designed for expression on a thermophilic bacterium cell surface. STUD includes a modified form of the TtoA protein from the organism *Thermus thermophilus*, or a conservative analog thereof, that results in the two ends of the mature TtoA protein joined via a linker, optionally a flexible linker, and a target protein or peptide is expressed at a non-wild type N- or C-terminal end that is positioned external to the outer membrane of the cell.

Figure 1A:
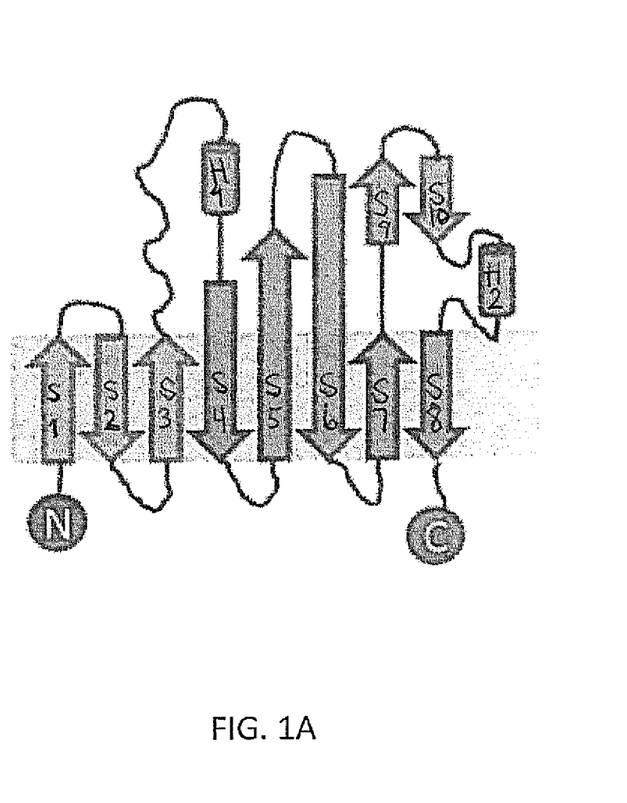
FIG. 1A illustrates a schematic of the TtoA protein from *T. thermophilus* illustrating the secondary structure membrane organization with the beta-strands numbered accordingly as S1, S2, S3, S4, S5, S6, S7, S8, S9 and S10 and the alpha-helices are numbered accordingly as H1 and H2.
Figure 1B:
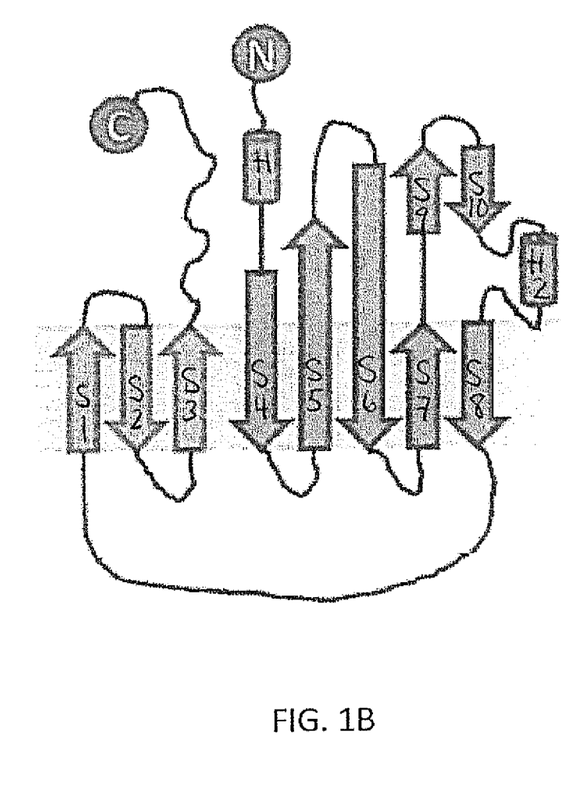
FIG. 1B illustrates a schematic of a STUD protein according to one aspect illustrating the secondary structure membrane organization with the beta-strands and helices numbered accordingly as in FIG. 1A.
Figure 2:
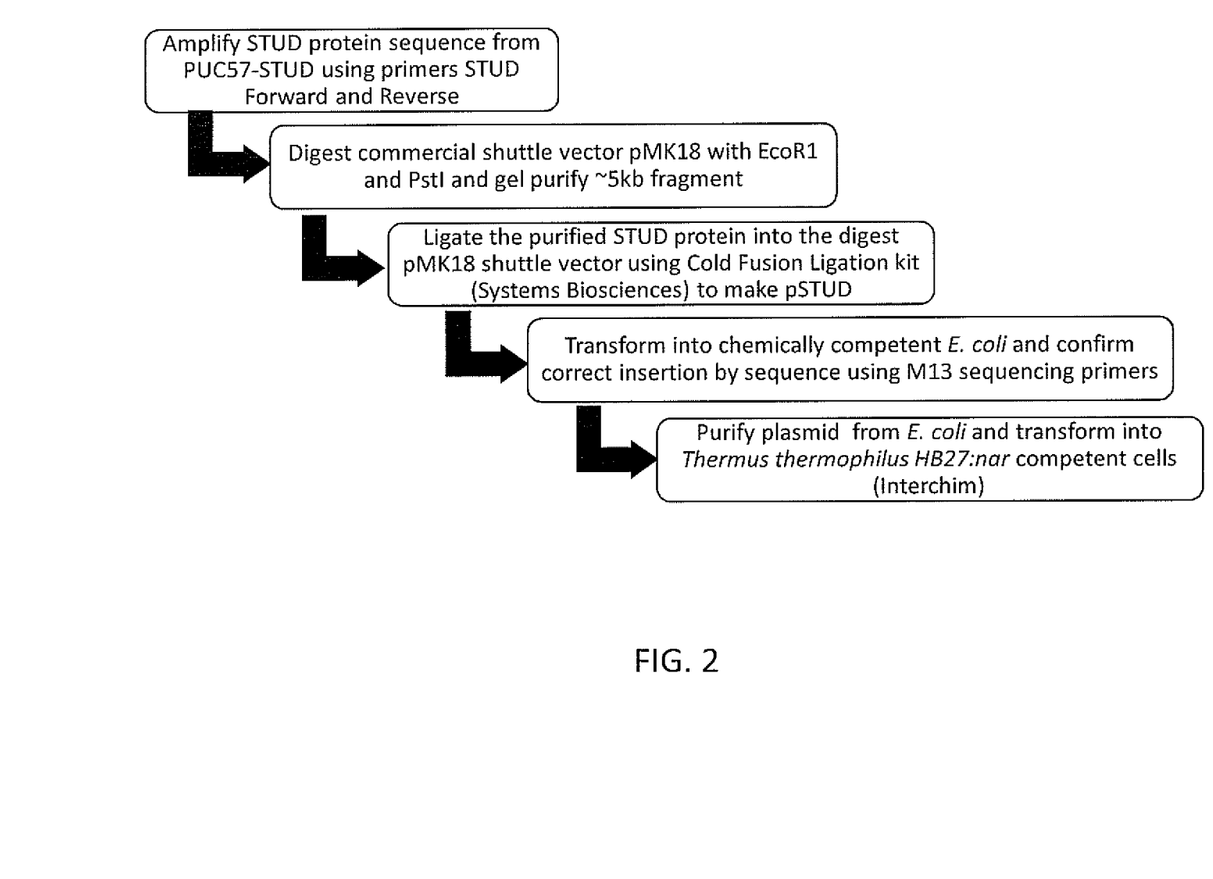
FIG. 2 illustrates a flow chart of one method of generating a STUD protein expression vector.

As such, a composition is provided that includes: a first peptide comprising a C-terminal sequence of a TtoA protein or conservative analog thereof; a second peptide comprising a N-terminal sequence of said TtoA protein or conservative analog thereof, whereby the first peptide is bound to the second peptide by an intermediate linker domain linking a C-terminus of the first peptide and a N-terminus of the second peptide. Thus, the wild-type TtoA protein is rearranged in primary sequence to allow a non-wild type terminus to be formed that will be positioned external to the cell membrane and to which a target peptide or protein may be attached. The linker serves to join the first and second peptides together. An exemplary schematic of a STUD protein is illustrated in FIG. 1 illustrating an aspect with similar folding and membrane arrangement to wild-type TtoA protein (FIG. 1A) but with one extracellular loop cleaved or missing to produce a new N-terminal and C-terminal end as well as a linker connecting the two ends of the STUD protein (FIG. 1B).

The STUD protein includes two or more contiguous amino acid sequences from the wild-type *T. thermophilus* TtoA protein or a conservative analog thereof. The amino acid sequence of the wild-type *T. thermophilus* TtoA protein including an N-terminal 6x-His tag is provided in SEQ ID NO: 1.

(SEQ ID NO: 1)
```
  1 qhhhhhhaak fsveagagfy ggfggqlavv aedlapglpl gvrlgvgfat sdalddgydl
 61 gggttwgdvk eagkfsewgq nvtlsldvly kpsglglpve vapyfgvryn ffsggytdpe
121 dnltikaqti ssnqlglglg vraayplmpn lslvgdlgvd yyfqacftrv eeddsgnksq
181 ssvcpgdsgy edvnkfvtqp ewvlklrlga ayrf
```

In some aspects, a first peptide includes a C-terminal sequence of a TtoA protein or conservative analog thereof. A C-terminal sequence of TtoA optionally includes the C-terminal residue of TtoA and optionally 5 or more residues contiguously N-terminal to the C-terminal residue of TtoA, optionally 5, 10, 15, 20, 25, 30, 35, 40, 45, 50, 55, 60, 65, 70, 75, 80, 85, 90, 95, 100, 105, 110, 115, 120, 125, 130, 135, 140, 140, 150, or more residues contiguously N-terminal to the C-terminal residue of TtoA, with the proviso that the first peptide excludes the mature or immature N-terminal amino acids of TtoA. In some aspects, a first peptide includes residues 64-214 of SEQ ID NO: 1, or a conservative analog thereof.

A second peptide includes a N-terminal sequence of the TtoA protein or conservative analog thereof. A N-terminal sequence of TtoA includes the N-terminal residue of mature TtoA protein, or within 20 amino acids C-terminal of the N-terminal residue, absent the signal peptide, and optionally 5 or more residues C-terminal to the N-terminal residue of TtoA, optionally 5, 10, 15, 20, 25, 30, 35, 40, 45, 50, 55, 60, 65, 70, 75, 80, 85, 90, 95, 100, 105, 110, 115, 120, 125, 130, 135, 140, 140, 150, or more residues contiguously C-terminal to the mature N-terminal residue of TtoA, with the provision that the second peptide excludes the C-terminal residue of mature TtoA. In some aspects, a second peptide includes residues 11-63 of SEQ ID NO: 1, or a conservative analog thereof.

The first peptide and the second peptide are bound by an intermediate linker domain. A linker domain is an amino acid sequence with from 3 to 60 contiguous amino acids, optionally 5 to 60, optionally 10 to 60, optionally 15 to 60 contiguous amino acids, optionally more than 60 contiguous amino acids. The maximum number of amino acids in a linker is fewer than the number of amino acids that will prevent proper in membrane folding and expression of the STUD protein. The linker domain optionally includes 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids. The sequence of the linker domain is optionally sufficient to provide a flexible link between the first and second peptides. In some aspects, a linker excludes amino acid sequences that result in membrane insertion so as to leave the entire linker on the intracellular or extracellular side of the cell membrane. In some aspects, a linker includes or is a sequence GGSGK (SEQ ID NO: 3).

A thermostable protein optionally includes a binding peptide. A binding peptide is optionally used for characterization of cell surface expression of a STUD protein, for purification of a STUD protein, for tagging a STUD protein, or other use. A binding peptide is optionally contiguous with the C-terminal or N-terminal end of the STUD protein. In some aspects, a binding peptide is inserted at a terminus or an internal section of a STUD protein. Optionally, a binding peptide is positioned at the opposite end of a STUD protein from a target peptide. A binding peptide optionally includes: a 6x-His tag; a P2X peptide for binding of an SHC domain of certain fluorophores such as Ypet-Mona; FLAG; ubiquitin; or other peptide tag known in the art. A binding peptide or portion thereof is illustratively cleavable such as by linking to STUD via an enzyme cleavage sequence that is cleavable by an enzyme known in the art illustratively including Factor Xa, thrombin, or trypsin. It is further appreciated that chemical cleavage is similarly operable with an appropriate cleavable linker. A binding peptide is optionally used to identify cells properly expressing STUD on the cell surface such as using specific labeling techniques illustratively fluorescent antibody labeling that is readily detectable using known techniques. Illustrative detection techniques include but are not limited to flow cytometry, bioluminescence, microscopy and other cell imaging techniques, microfluidic binding assays such as those described by Kumar et al., *Lab Chip*, 2012; 12:1646-1655, surface plasmon resonance such as that described by Shabot, et al., *Biosens Bioelectron.* 2009; 24(6):1667-73, cell lysis and immunoprecipitation methods, among others known in the art.

A thermostable protein optionally includes a target peptide. A target peptide is an amino acid sequence, optionally from 4 to 100 amino acids in length of known or unknown sequence, structure, affinity, or other parameter. A target peptide is optionally a peptide component of a peptide library that includes two or more peptides. Peptide libraries and their uses are well known in the art. The STUD protein has utility to express a target peptide on the surface of a cell, optionally a thermophilic cell, under conditions that render other expression systems inoperable, illustratively at temperatures of 60° C. to 98° C. A target peptide is optionally linked to a STUD protein by a peptide bond and is optionally expressed intermediate a signal peptide and a mature STUD protein sequence such that upon cleavage of the signal peptide, the target peptide sequence is expressed on the N-terminus of the STUD protein in a region external to the cell membrane for exposure to the extracellular environment. It is appreciated, however, that in some aspects, a target peptide is bonded to the C-terminus of the STUD protein.

The thermostable protein useful as a STUD protein optionally has a first peptide including residues 64-214 of SEQ ID NO: 1, or a conservative analog thereof, and a second peptide including residues 11-63 of SEQ ID NO: 1, or a conservative analog thereof. In some aspects a thermostable protein includes the sequence of (SEQ ID NO: 2)
MKKGLLAALAGFLTLAMAQGTVDTTWGDVKEAGKFSEWGQNVTLSLDVLY

KPSGLGLPVEVAPYFGVRYNFFSGGYTDPEDNLTIKAQTISSNQLGLGLG

VRAAYPLMPNLSLVGDLGVDYYFQACFTRVEEDDSGNKSQSSVCPGDSGY

EDVNKFVTQPEWVLKLRLGAAYRFGGSGKFSVEAGAGFYGGFGGQLAVVA

EDLAPGLPLGVRLGVGFATSDALDDGYDLGGGHISQWKPKVPNREDKYKK.

A STUD protein optionally includes a β-barrel structure encompassing at least a portion of the STUD protein when expressed within a cell membrane. Without being limited to one particular theory, it is believed that the presence of the β-barrel structure improves thermal stability of the resulting STUD protein. As such, some aspects include a STUD protein that include such a structure to promote increased thermal stability relative to a STUD protein that does not form a β-barrel structure.

A STUD protein optionally includes conservative analogues of one or more regions of the TtoA protein of *T. thermophilus*. As defined herein a conservative analog includes one or more amino acid substitutions, deletions, additions, or modifications (e.g. glycosylation, phosphorylation, sulfation, label, or other) that does not substantially alter a function, expression, folding, membrane arrangement, expression, or other biological, chemical or physical characteristic of the STUD protein of SEQ ID NO: 2. In some aspects a conservative analog exhibits at least about 50% percent identity, more preferably at least about 80%, and even more preferably between about 85% and 99% (or any value therebetween) to the sequence from which it is derived. Such conservative analogues can include posttranslational modifications of the protein or peptide, for example, glycosylation, acetylation, phosphorylation, and the like.

In some aspects, residues 201-208 of SEQ ID NO: 2 include one or more substitutions, deletions, or modifications. Optionally, any one or more of residues 201-208 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 201-208 of SEQ ID NO: 2 are deleted. Optionally, 1, 2, 3, 4, 5, 6, or 7 residues are deleted. Optionally, one or more residues are added to residues 201-208 of SEQ ID NO: 2 either internally, or on the terminus of residues 201-208 of SEQ ID NO: 2. Optionally, 1, 2, 3, 4, 5, 6, 7, or more residues are added.

In some aspects, residues 51-59 of SEQ ID NO: 2 include one or more substitutions, deletions, or modifications. Optionally, any one or more of residues 51-59 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 51-59 of SEQ ID NO: 2 are deleted. Optionally, 1, 2, 3, 4, 5, 6, 7, or 8 residues are deleted. Optionally, one or more residues are added to residues 51-59 of SEQ ID NO: 2 either internally, or on the terminus of residues 51-59 of SEQ ID NO: 2. Optionally, 1, 2, 3, 4, 5, 6, 7, or more residues are added.

In some aspects, residues 109-110 of SEQ ID NO: 2 include one or more substitutions, deletions, or modifications. Optionally, any one or more of residues 109-110 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 109-110 of SEQ ID NO: 2 are deleted. Optionally, 1 or 2 residues are deleted. Optionally, one or more residues are added to residues 109-110 of SEQ ID NO: 2 either internally, or on the terminus of residues 109-110 of SEQ ID NO: 2. Optionally, 1, 2, 3, 4, 5, 6, 7, or more residues are added.

In some aspects, residues 121-161 of SEQ ID NO: 2 include one or more substitutions, deletions, or modifications. Optionally, any one or more of residues 121-161 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 121-161 of SEQ ID NO: 2 are deleted. Optionally, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues are deleted. Optionally, one or more residues are added to residues 121-161 of SEQ ID NO: 2 either internally, or on the terminus of residues 121-161 of SEQ ID NO: 2. Optionally, 1, 2, 3, 4, 5, 6, 7, or more residues are added.

In some aspects, residues 79-85 of SEQ ID NO: 2 include one or more substitutions, deletions, or modifications. Optionally, any one or more of residues 79-85 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 79-85 of SEQ ID NO: 2 are deleted. Optionally, 1, 2, 3, 4, 5, 6, or 7 residues are deleted. Optionally, one or more residues are added to residues 79-85 of SEQ ID NO: 2 either internally, or on the terminus of residues 79-85 of SEQ ID NO: 2. Optionally, 1, 2, 3, 4, 5, 6, 7, or more residues are added.

In some aspects, residues 193-194 of SEQ ID NO: 2 include one or more substitutions, deletions, or modifications. Optionally, any one or more of residues 193-194 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, l-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 193-194 of SEQ ID NO: 2 are deleted. Optionally, 1 or 2 residues are deleted. Optionally, one or more residues are added to residues 193-194 of SEQ ID NO: 2 either internally, or on the terminus of residues 193-194 of SEQ ID NO: 2. Optionally, 1, 2, 3, 4, 5, 6, 7, or more residues are added.

In some aspects, residues 220-232 of SEQ ID NO: 2 include one or more substitutions, deletions, or modifications. Optionally, any one or more of residues 220-232 is substituted to an alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, l-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, or 2-naphthylalanine. Optionally, one or more of residues 220-232 of SEQ ID NO: 2 are deleted. Optionally, 1, 2, 3, 4, 5, 6, 7, 8, 9, 10, 11, or 12 residues are deleted. Optionally, one or more residues are added to residues 220-232 of SEQ ID NO: 2 either internally, or on the terminus of residues 220-232 of SEQ ID NO: 2. Optionally, 1, 2, 3, 4, 5, 6, 7, or more residues are added.

In some aspects, a conservative analog includes a substitution, deletion, or addition to an amino acid sequence other than residues 201-208, 51-59, 109-110, 121-161, 79-85, 193-194, or 220-232 of SEQ ID NO: 2. Such conservative analogues to such regions are optionally conservative substitutions illustratively including but not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

In making conservative analogs, the hydropathic index of amino acids can be considered. The importance of the hydropathic amino acid index in conferring interactive biologic function on a protein or peptide is generally understood in the art. It is known that certain amino acids can be substituted for other amino acids having a similar hydropathic index or score and still result in a protein or peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein or peptide, which in turn defines the interaction of the protein or peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 are optional, those within ±1 are optional preferred, and those within ±0.5 are optional.

Substitution of like amino acids can also be made on the basis of hydrophilicity, particularly, where the biological functional equivalent protein or peptide thereby created is intended for use in immunological aspects. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein or peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Aspects of this disclosure, thus, contemplate functional or biological equivalents of a protein or peptide as set forth above. In particular, aspects of the protein or peptide can include variants having about 50%, 60%, 70%, 80%, 90%, and 95% sequence identity to the STUD amino acid sequence of SEQ ID NO: 2.

It is recognized that numerous conservative analogs are within the scope of the present invention including amino acid substitutions, alterations, modifications, or other amino acid changes that increase, decrease, or do not alter the function of the STUD protein sequence of SEQ ID NO: 2. Several post-translational modifications are similarly envisioned as within the scope of the present invention illustratively including incorporation of a non-naturally occurring amino acid, phosphorylation, glycosylation, addition of pendent groups such as biotinylation, fluorophores, lumiphores, radioactive groups, antigens, or other molecules.

As one example of a non-conservative mutation, a proline often destroys α-helical structure. As such, a proline substitution within a region of a STUD protein that assumes an α-helix is optionally excluded.

A STUD protein is appreciated as recombinantly expressed as the protein is not found in nature. As such, a vector is provided that includes a nucleic acid sequence encoding a STUD protein. Illustrative vectors include a plasmid, cosmid, cationic lipids, non-liposomal cationic vectors, cationic cyclodextrin, viruses with RNA or DNA genetic material, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker, optionally an antibiotic resistance gene.

As such, a vector optionally includes or is a nucleic acid sequence of contiguous nucleotides that encode a STUD protein. It is appreciated that a nucleic acid sequence is readily envisioned by one of ordinary skill in the art from a corresponding amino acid sequence. In some aspects, a vector includes a nucleic acid sequence of SEQ ID NO: 3. In some aspects, conservative mutations in the amino acid sequence of SEQ ID NO: 3 are also provided. Illustrative examples of conservative mutations include those that do not alter the amino acid encoded by the codon housing the mutation and those that encode conservative analogs of the STUD protein sequence.

The term "nucleotide" is intended to mean a base-sugar-phosphate combination either natural or synthetic. Included in this definition are modified nucleotides which include additions to the sugar-phosphate groups as well as to the bases. Natural nucleotides include adenine, guanine, thymine, cytosine, and uracil.

The term "nucleic acid" or "oligonucleotide" refers to multiple nucleotides attached in the form of a single or double stranded polynucleotide that can be natural, or derived synthetically, enzymatically, and by cloning methods.

Numerous methods are known in the art for the synthesis and production of nucleic acid sequences that can be used to introduce a nucleic acid sequence encoding a STUD protein into an expression vector. A nucleic acid encoding a STUD protein may be synthetically synthesized by techniques known in the art, illustratively, solid phase synthesis using a phosphoramidite method, by selectively cloning and amplifying various oligonucleotide sequences encoding a desired protein or peptide and splicing desired sequences together by methods known in the art (e.g. blunt end ligation, ligation of like restriction sites, etc.). The synthesized sequence may then be inserted (optionally following amplification) into the vector by recombination methods known in the art. A nucleic acid is optionally amplified by a polymerase chain reaction (PCR) by techniques known in the art and as described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many PCR processes are known to those of skill in the art and may be used to amplify a nucleic acid sequence. The parameters of PCR cycling times, temperature, and number of steps are dependent on the primer pair, their melting temperature, and other considerations understood by those of ordinary skill in the art. It is appreciated that optimizing PCR parameters for various probe sets is well within the skill of the art and is performed as mere routine optimization.

The term "amplifying," "amplified," or "amplification" defines the process of making multiple copies of the nucleic acid from a single or lower copy number of nucleic acid sequence molecule. The amplification of nucleic acid sequences is carried out in vitro by biochemical processes known to those of skill in the art. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In a preferred aspect, the enzyme is hot-start iTaq DNA polymerase from Bio-rad (Hercules, Calif.). Suitable enzymes will facilitate combination of the nucleotides in the proper manner to form the primer extension products that are complementary to each nucleic acid strand. Generally, the synthesis is initiated at the 3'-end of each primer and proceeds in the 5'-direction along the template strand, until synthesis terminates. There may be amplification agents, however, that initiate synthesis at the 5'-end and proceed in the other direction, using the same process as described above. In any event, the process of the invention is not to be limited to the aspects of amplification described herein.

Optionally, a nucleic acid encoding a STUD protein is engineered into an expression or other plasmid for storage, expansion, expression or other use. A plasmid is any plasmid suitable for housing a STUD nucleic acid sequence or for producing protein expression in a thermophilic organism, optionally T. thermophilus. Examples of such plasmids are commercially available and include pUC57 and pMK18. One method of introducing a nucleic acid encoding a STUD protein into a vector includes custom synthesis of the STUD sequence in a pUC57 vector by standard commercially available methods offered by vendors. The STUD is optionally amplified from the pUC57 synthesis vector using primers suitable for such amplification. In some aspects such as for the expression of the nucleic acid of SEQ ID NO: 3, the forward primer

```
GGAGGAGCAGCAGAATTCAC     (SEQ ID NO: 5)
``` and reverse primer

```
TGCTGCTCCTCCCTGC         (SEQ ID NO: 6)
``` are used with commercially available PCR amplification products and purification techniques. Primers are complementary in whole or in part to one or more strands of nucleic acid sequence to be amplified. The term "complementary" means that the primers must hybridize with their respective strand under conditions that allow the agent for polymerization to function. In other words, the primers that are complementary to the flanking sequences hybridize with the flanking sequences and permit amplification of the nucleotide sequence. Preferably, the 3' terminus of the primer that is extended is perfectly base paired with the complementary flanking strand.

Figure 3:
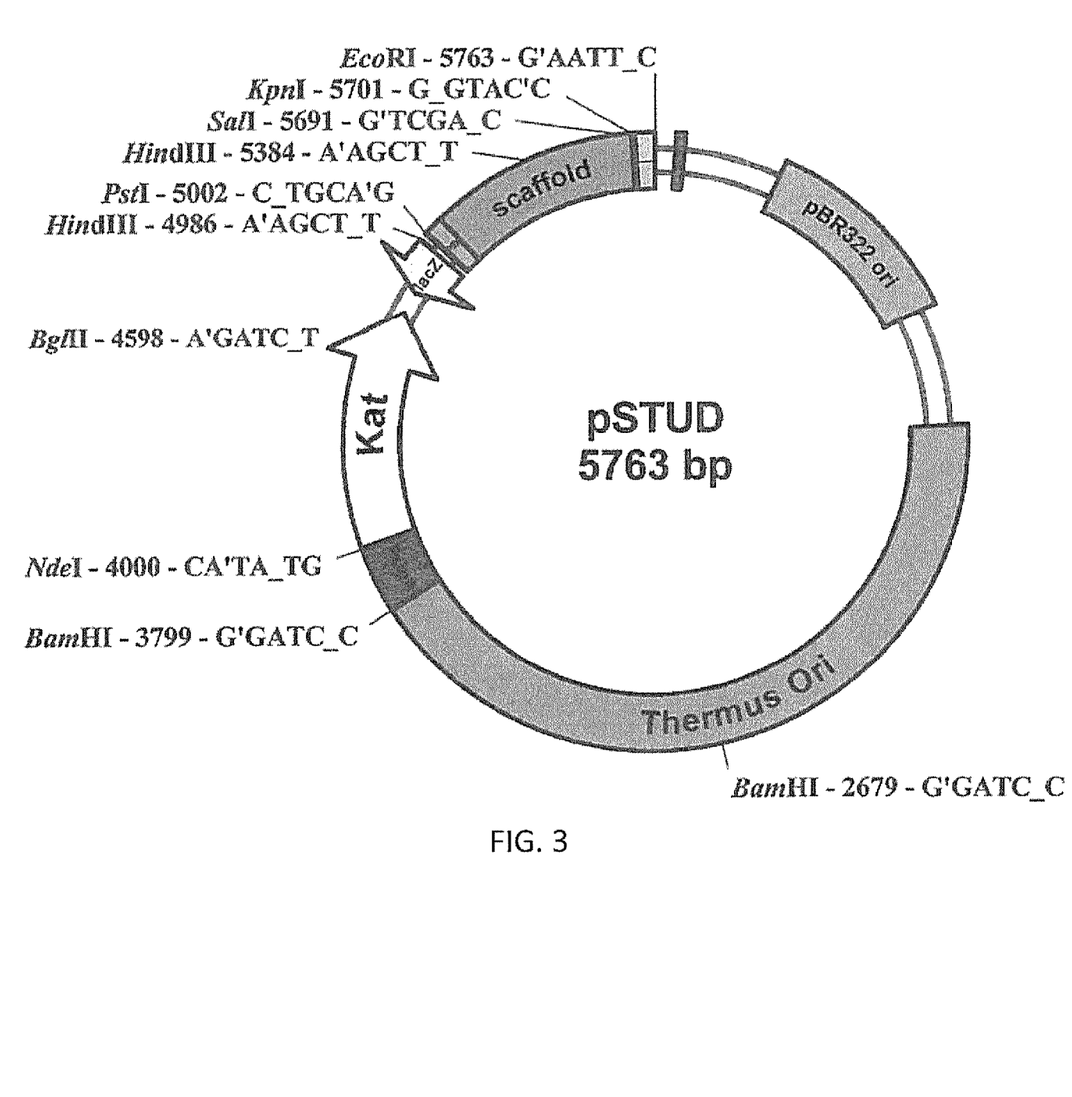
FIG. 3 illustrates a vector encoding a STUD protein according to one aspect.

A vector optionally includes one or more sequences for regulated expression, growth, or expression of a protein encoded by the vector. One illustrative example of an expression vector uses the pMK18 plasmid from Biotools. The amplified STUD nucleic acid sequence is optionally inserted into the vector as shown in FIG. 3. The pMK18 is digested with restriction enzymes, optionally EcoR1-HF and Pst1-HF (New England Biolabs), and then purified by agarose gel electrophoresis separation followed by gel extraction. The STUD protein gene is inserted into the digested pMK18 vector using a cold fusion ligation reaction and transformed into chemically competent E. coli cells. After incubation on LB kanamycin agar plates overnight, selected colonies are sequenced using the M13 commercial sequencing primer to verify the presence of the STUD protein genetic sequence. After cloning is complete, the STUD gene will be located downstream of a lac promoter, allowing expression to be induced by IPTG. It is appreciated that other plasmid vectors including other expression, multiplication, selection, or other parameter, control elements are similarly suitable and may be tailored to the organism desired for storage, expansion, expression, or selection.

Also provided is a host cell transformed with an appropriate vector or with a nucleic acid sequence encoding a STUD protein. Illustrative examples of a host cell include E. coli and any thermophilic organism, optionally T. thermophilus. Optionally, a host organism is capable of protein expression at temperatures unsuitable for most bacterial organisms, optionally in excess of 60° C., optionally from 60° C. to 98° C. Optionally, a vector encoding a STUD protein is introduced into a cell by cell transfection optionally achieved by electroporation, chemical transformation such as with the use of divalent cations (e.g. calcium chloride), heat shock, or combinations thereof. Numerous agents are amenable to facilitate cell transfection illustratively including synthetic or natural transfection agents such as LIPOFECTIN, baculovirus, naked plasmid or other DNA, or other systems known in the art.

Also provided is a peptide library. The term "peptide" as used herein with regard to libraries, is intended to include molecules comprised of natural or synthetic amino acid residues (i.e., alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine) linked by peptide bonds, or other residues that can optionally be determined by standard sequencing methodologies (e.g., direct sequencing of the amino acids making up the peptides or sequencing of nucleic acid molecules encoding the peptide). A peptide library is a multiplicity of peptides where each peptide is linked to a STUD protein during expression, or the nucleic acid encoding the peptide is linked to a nucleic acid sequence encoding a STUD protein. A "multiplicity" is understood as a plurality of peptides of random or non-random sequence of amino acids or derivatives thereof. Thus a "library comprising a multiplicity of peptides" refers to a library of peptides including at least two different peptide members. Optionally, libraries of peptides include at least $10^3$ different peptides, optionally at least $10^6$ different peptides, optionally at least about $10^9$ different peptides. Depending on the length of the peptide members and the efficiency of synthesis, library diversity as high as $10^{12}$ different peptides or even $10^{15}$ different peptides. A peptide optionally includes 2 to 5000 contiguous amino acids, or any value or range therebetween. Optionally, peptides have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids.

Figure 4:
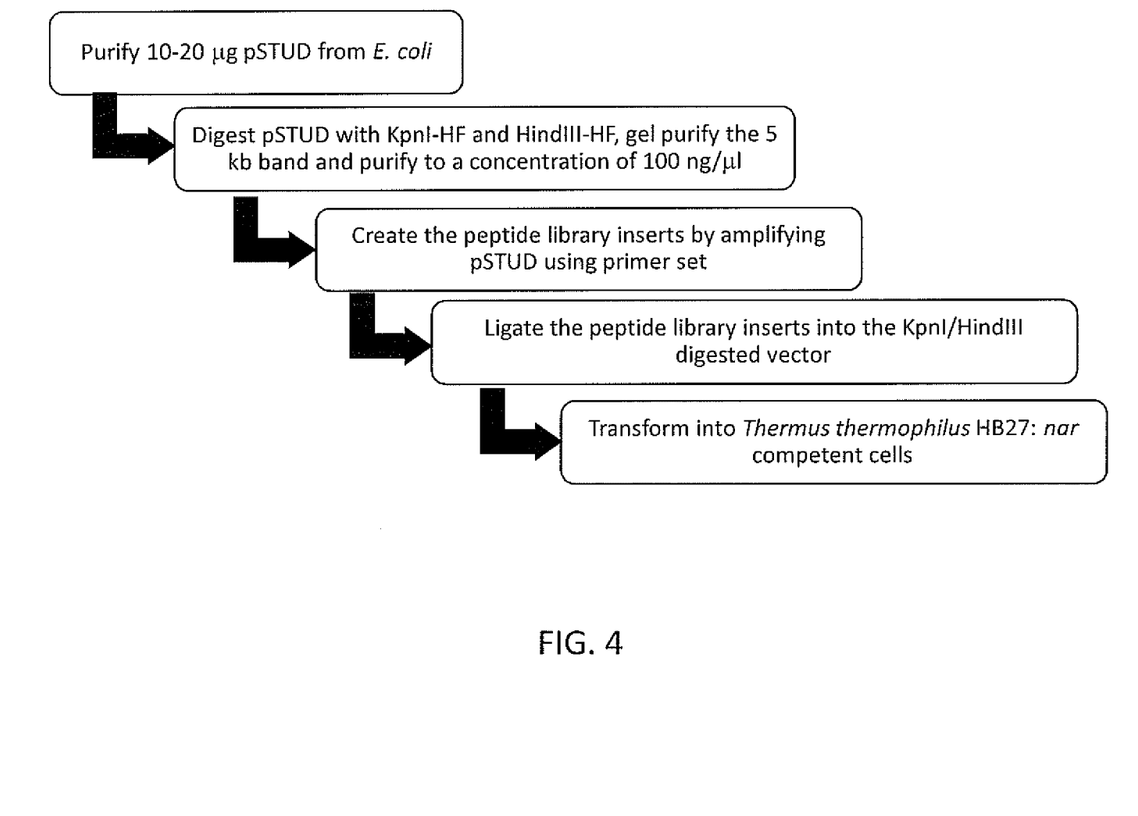
FIG. 4 illustrates a flow chart of one method of creating a peptide library using the STUD protein and vector encoding the STUD protein.
Figure 5:
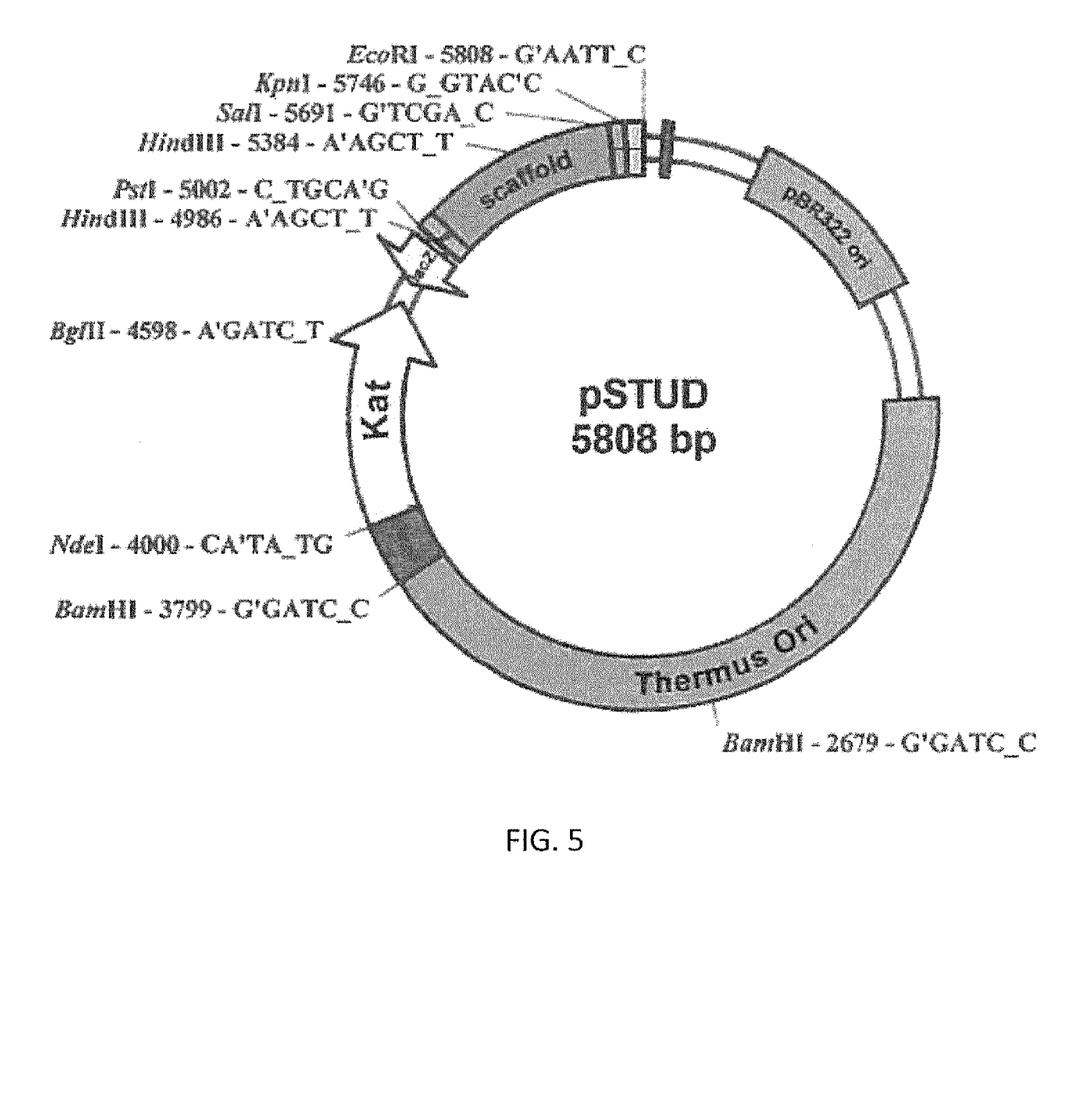
FIG. 5 illustrates a vector housing a nucleic acid sequence encoding a STUD protein ligated to a target peptide according to one aspect.

One exemplary method of forming a peptide library involves the creation of two or more sequences encoding target peptides within the STUD scaffold substantially as illustrated in FIG. 4. A 15-mer peptide example is described here, but other peptide lengths ranging in size from 5 amino acids to 50 amino acids or more may be constructed using the same method and displayed on the N-terminus of the STUD protein. 10-20 μg of pSTUD (as shown in FIG. 3) is purified from E. coli using commercial plasmid purification kits. To create a peptide library, pSTUD is digested with KpnI-HF and HindIII-HF (NEB) and purified by agarose gel electrophoresis separation followed by gel extraction to a concentration of 200 ng/pt. The 15-mer peptide library is generated by amplifying the intact pSTUD vector using a forward degenerate primer (SEQ ID NO: 7)
5'-GGTACCCTGCGCCATAGCTATGGCGCAGGGTACCNNSNNSNNSNNSN

NSNNSNNSNNSNNSNNSNNSNNSNNSNNSNNSGTCGACACTACCTGGGGT

GATG-3' and the reverse primer

5'-TGCAGTTATTACTTCTTG-3'      (SEQ ID NO: 8)

using commercial PCR amplification products and purification techniques. The forward primer includes a leader sequence encoding the signal peptide for STUD to be inserted into the cell membrane upon expression and is subsequently cleaved off following expression. In order to construct the pSTUD-library (FIG. 4), the library PCR products are ligated into the previously digested pSTUD vector and transformed into T. thermophilus HB27:nar competent cells (Biotools). Alternatively, a QUIKCHANGE LIGHTNING MUTAGENESIS kit may be used in conjunction with the degenerate primer set described above to initiate replication of pSTUD, thus incorporating the 15-mer peptide genetic sequence in the replicated vector. DpnI digestion may be used to remove the template from the library before transforming the library into a host cell such as E. coli, or T. thermophilus.

Figure 6:
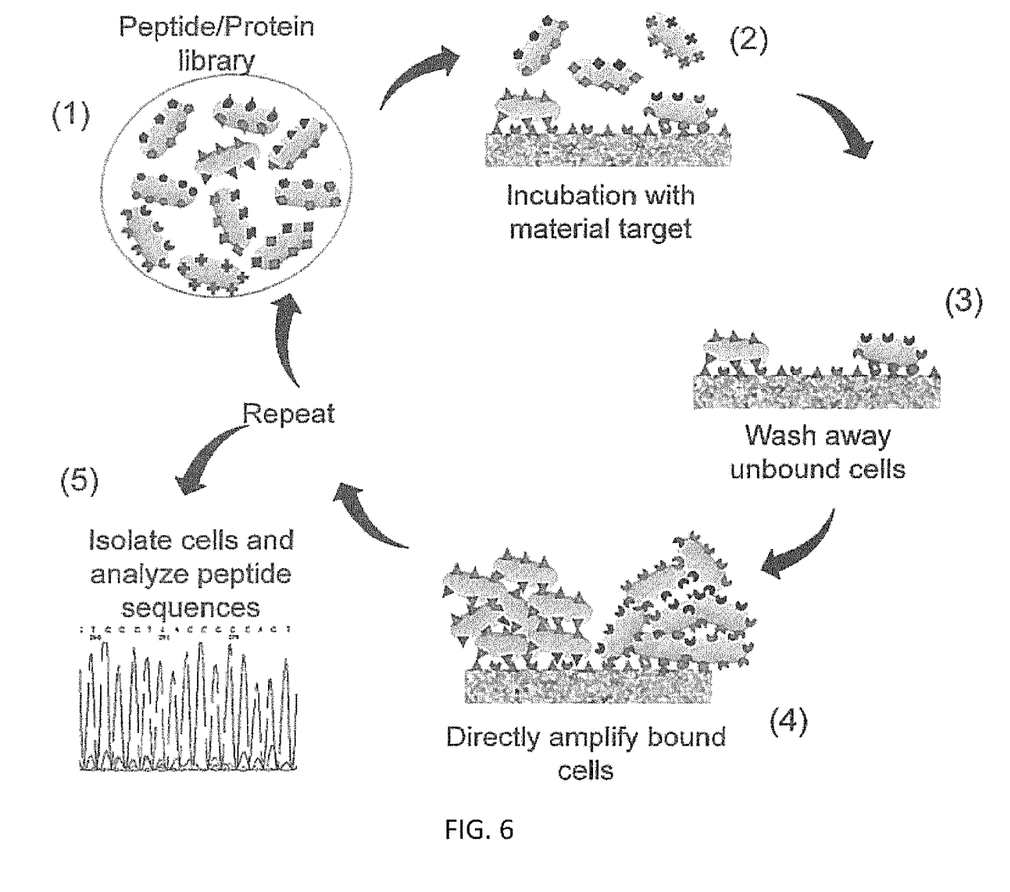
FIG. 6 illustrates a schematic of one exemplary process of identifying a target peptide using a STUD protein.

The resulting peptide library can be used in screening processes for the identification of peptides with descried structural or functional characteristics by techniques similar to those used for other bacterial peptide library screening systems with the notable exceptions that the present system if far more robust in being capable of expression at elevated temperatures such as those at or in excess of 60° C. and up to 98° C. A generalized biopanning method for the identification of target peptide with the desired characteristics from a STUD-based library in T. thermophilus is illustrated in FIG. 6. Briefly, the library is inoculated into fresh media, grown up, and then protein expression induced with IPTG. After induction, cells are chilled on ice before the addition of the target material at the desired temperature (4-98° C.), thus becoming a first round sort. The library is incubated with the target and then loosely bound or unbound cells are washed away. Those cells displaying a protein or peptide that interacts with the target are then amplified by a re-growth step in fresh media at 70° C. This cell population is then used in a second round of sorting and the induction, incubation, washing, and regrowth regime is repeated. This is optionally repeated 3-4 times before the final population is selected. After the final round of sorting, the re-growth population in cultured on solid media and colonies selected. Through DNA sequencing analysis of the STUD protein gene, the protein or peptide sequence can be readily determined.

As such, the compositions and processes described herein this invention are useful for biomaterial discovery (e.g. biopanning) for peptide/protein biomaterial development and study at biological thermal extremes (4-98° C.), each achievable for the first time using the STUD protein and vectors encoding it. The present system will enable high temperature protein and peptide display, similar to phage display technology but at temperatures greater than 60° C. (and up to 98° C.). As such, the compositions and processes represent a new toolset for study, discovery and development of a broad range of materials, with direct impact to many single- and dual-use applications.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, N Y, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, N Y, 1991; and Methods of Immunological Analysis, ed. Masseyeff et al., John Wiley & Sons, N Y, 1992.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular aspects of the invention, but is not meant to be a limitation upon the practice thereof. The following claims, including all equivalents thereof, are intended to define the scope of the invention.

We claim:

1. A thermostable TtoA protein comprising: a first peptide comprising a wild-type TtoA sequence or conservative analog thereof which comprises from the N-terminus to C-terminus the secondary structural elements: H1-S4-S5-S6-S7-S9-S10-H2-S8 linked at the C-terminus to a second TtoA peptide by an intermediate linker domain, wherein said second peptide comprises from the N-terminus to C-terminus a TtoA wild-type sequence or conservative analog thereof comprising the secondary structural elements S1-S2-S3, wherein H's are alpha-helices and S's are beta-strands.

2. The protein of claim 1, said first peptide comprising residues 64-214 of SEQ ID NO: 1, or a conservative analog thereof.

3. The protein of claim 1, said second peptide comprising residues 11-63 of SEQ ID NO: 1, or a conservative analog thereof.

4. The protein of claim 1, further comprising a signal peptide associated with a N-terminus of said first peptide.

5. The protein of claim 1, further comprising a binding peptide associated with a C-terminus of said second peptide.

6. The protein of claim 5, wherein said binding peptide is a P2X peptide.

7. The protein of claim 1, wherein said linker domain comprises an amino acid.

8. The protein of claim 1, wherein said linker domain comprises 2-40 amino acids.

9. The protein of claim 1, comprising SEQ ID NO: 2 or conservative analog thereof.

* * * * *

SEQUENCE LISTING

```
<160> NUMBER OF SEQ ID NOS: 8

<210> SEQ ID NO 1
<211> LENGTH: 214
<212> TYPE: PRT
<213> ORGANISM: Thermus thermophilus

<400> SEQUENCE: 1

Gln His His His His His Ala Ala Lys Phe Ser Val Glu Ala Gly
1               5                   10                  15

Ala Gly Phe Tyr Gly Gly Phe Gly Gly Gln Leu Ala Val Val Ala Glu
            20                  25                  30

Asp Leu Ala Pro Gly Leu Pro Leu Gly Val Arg Leu Gly Val Gly Phe
        35                  40                  45

Ala Thr Ser Asp Ala Leu Asp Asp Gly Tyr Asp Leu Gly Gly Gly Thr
    50                  55                  60

Thr Trp Gly Asp Val Lys Glu Ala Gly Lys Phe Ser Glu Trp Gly Gln
65                  70                  75                  80

Asn Val Thr Leu Ser Leu Asp Val Leu Tyr Lys Pro Ser Gly Leu Gly
                85                  90                  95

Leu Pro Val Glu Val Ala Pro Tyr Phe Gly Val Arg Tyr Asn Phe Phe
            100                 105                 110

Ser Gly Gly Tyr Thr Asp Pro Glu Asp Asn Leu Thr Ile Lys Ala Gln
        115                 120                 125

Thr Ile Ser Ser Asn Gln Leu Gly Leu Gly Leu Gly Val Arg Ala Ala
    130                 135                 140

Tyr Pro Leu Met Pro Asn Leu Ser Leu Val Gly Asp Leu Gly Val Asp
145                 150                 155                 160

Tyr Tyr Phe Gln Ala Cys Phe Thr Arg Val Glu Glu Asp Asp Ser Gly
```

```
                        165                 170                 175
Asn Lys Ser Gln Ser Ser Val Cys Pro Gly Asp Ser Gly Tyr Glu Asp
            180                 185                 190

Val Asn Lys Phe Val Thr Gln Pro Glu Trp Val Leu Lys Leu Arg Leu
        195                 200                 205

Gly Ala Ala Tyr Arg Phe
    210

<210> SEQ ID NO 2
<211> LENGTH: 250
<212> TYPE: PRT
<213> ORGANISM: Artificial Sequence
<220> FEATURE:
<223> OTHER INFORMATION: Synthetic protein

<400> SEQUENCE: 2

Met Lys Lys Gly Leu Leu Ala Ala Leu Ala Gly Phe Leu Thr Leu Ala
1               5                   10                  15

Met Ala Gln Gly Thr Val Asp Thr Thr Trp Gly Asp Val Lys Glu Ala
            20                  25                  30

Gly Lys Phe Ser Glu Trp Gly Gln Asn Val Thr Leu Ser Leu Asp Val
        35                  40                  45

Leu Tyr Lys Pro Ser Gly Leu Gly Leu Pro Val Glu Val Ala Pro Tyr
    50                  55                  60

Phe Gly Val Arg Tyr Asn Phe Phe Ser Gly Gly Tyr Thr Asp Pro Glu
65                  70                  75                  80

Asp Asn Leu Thr Ile Lys Ala Gln Thr Ile Ser Ser Asn Gln Leu Gly
            85                  90                  95

Leu Gly Leu Gly Val Arg Ala Ala Tyr Pro Leu Met Pro Asn Leu Ser
        100                 105                 110

Leu Val Gly Asp Leu Gly Val Asp Tyr Tyr Phe Gln Ala Cys Phe Thr
    115                 120                 125

Arg Val Glu Glu Asp Asp Ser Gly Asn Lys Ser Gln Ser Ser Val Cys
130                 135                 140

Pro Gly Asp Ser Gly Tyr Glu Asp Val Asn Lys Phe Val Thr Gln Pro
145                 150                 155                 160

Glu Trp Val Leu Lys Leu Arg Leu Gly Ala Ala Tyr Arg Phe Gly Gly
            165                 170                 175

Ser Gly Lys Phe Ser Val Glu Ala Gly Ala Gly Phe Tyr Gly Gly Phe
        180                 185                 190

Gly Gly Gln Leu Ala Val Ala Glu Asp Leu Ala Pro Gly Leu Pro
    195                 200                 205

Leu Gly Val Arg Leu Gly Val Gly Phe Ala Thr Ser Asp Ala Leu Asp
    210                 215                 220

Asp Gly Tyr Asp Leu Gly Gly His Ile Ser Gln Trp Lys Pro Lys
225                 230                 235                 240

Val Pro Asn Arg Glu Asp Lys Tyr Lys Lys
            245                 250

<210> SEQ ID NO 3
<211> LENGTH: 5
<212> TYPE: PRT
<213> ORGANISM: Artificial Sequence
<220> FEATURE:
<223> OTHER INFORMATION: Synthetic protein

<400> SEQUENCE: 3
```

Gly Gly Ser Gly Lys
1               5

<210> SEQ ID NO 4
<211> LENGTH: 756
<212> TYPE: DNA
<213> ORGANISM: Artificial Sequence
<220> FEATURE:
<223> OTHER INFORMATION: Synthetic nucleic acid sequence

<400> SEQUENCE: 4

```
atgaagaagg gtcttttggc ggctctggca gggttcttga ccttagctat ggcgcagggt    60
accgtcgaca ctacctgggg tgatgtcaag gaggctggta agttctccga gtggggccag   120
aacgtcaccc tgtccctgga cgttctctac aagccgagcg gcctgggcct gccggtagag   180
gtagctccct acttcggcgt ccggtacaac ttcttctccg gtggctatac cgatcctgaa   240
gataacttaa cgattaaagc tcagacgatt tcttccaacc agctcggctt gggcctcggc   300
gtccgggccg cctacccctt gatgcccaac ctgagcctgg taggggacct ggggggtggac   360
tactacttcc aagcttgctt tacgcgcgta gaagaagacg atagcggtaa caaaagccag   420
agctccgttt gccccggtga cagtgggtac gaagacgtca acaagttcgt cacccagccc   480
gagtgggtgc tcaagctccg gctggggggcg gcctatcggt tcggcgggag tggcaagttc   540
tctgtagagg cggggggctgg tttctacggc ggcttcggag gccagctcgc ggtggtggcc   600
gaggacctgg ctccggggct tcccttgggt gtgcggttgg gggtggggtt tgccaccagc   660
gatgccctgg atgacggtta tgacctgggt ggcggtcaca tcagccagtg gaagccgaag   720
gtcccgaacc gcgaggacaa atacaagaag taataa                              756
```

<210> SEQ ID NO 5
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 5

```
ggaggagcag cagaattcac                                                 20
```

<210> SEQ ID NO 6
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 6

```
tgctgctcct ccctgc                                                     16
```

<210> SEQ ID NO 7
<211> LENGTH: 101
<212> TYPE: DNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: misc_feature
<222> LOCATION: (38)..(39)
<223> OTHER INFORMATION: n is a, c, g, t or u
<220> FEATURE:

```
<221> NAME/KEY: misc_feature
<222> LOCATION: (41)..(42)
<223> OTHER INFORMATION: n is a, c, g, t or u
<220> FEATURE:
<221> NAME/KEY: misc_feature
<222> LOCATION: (44)..(45)
<223> OTHER INFORMATION: n is a, c, g, t or u
<220> FEATURE:
<221> NAME/KEY: misc_feature
<222> LOCATION: (47)..(48)
<223> OTHER INFORMATION: n is a, c, g, t or u
<220> FEATURE:
<221> NAME/KEY: misc_feature
<222> LOCATION: (50)..(51)
<223> OTHER INFORMATION: n is a, c, g, t or u
<220> FEATURE:
<221> NAME/KEY: misc_feature
<222> LOCATION: (53)..(54)
<223> OTHER INFORMATION: n is a, c, g, t or u
<220> FEATURE:
<221> NAME/KEY: misc_feature
<222> LOCATION: (56)..(57)
<223> OTHER INFORMATION: n is a, c, g, t or u
<220> FEATURE:
<221> NAME/KEY: misc_feature
<222> LOCATION: (59)..(60)
<223> OTHER INFORMATION: n is a, c, g, t or u
<220> FEATURE:
<221> NAME/KEY: misc_feature
<222> LOCATION: (62)..(63)
<223> OTHER INFORMATION: n is a, c, g, t or u
<220> FEATURE:
<221> NAME/KEY: misc_feature
<222> LOCATION: (65)..(66)
<223> OTHER INFORMATION: n is a, c, g, t or u
<220> FEATURE:
<221> NAME/KEY: misc_feature
<222> LOCATION: (68)..(69)
<223> OTHER INFORMATION: n is a, c, g, t or u
<220> FEATURE:
<221> NAME/KEY: misc_feature
<222> LOCATION: (71)..(72)
<223> OTHER INFORMATION: n is a, c, g, t or u
<220> FEATURE:
<221> NAME/KEY: misc_feature
<222> LOCATION: (74)..(75)
<223> OTHER INFORMATION: n is a, c, g, t or u
<220> FEATURE:
<221> NAME/KEY: misc_feature
<222> LOCATION: (77)..(78)
<223> OTHER INFORMATION: n is a, c, g, t or u

<400> SEQUENCE: 7
ggtaccctgc gccatagcta tggcgcaggg taccnnsnns nnsnnsnnsn nsnnsnnsnn      60
snnsnnsnns nnsnnsnnsg tcgacactac ctggggtgat g                        101

<210> SEQ ID NO 8
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 8
tgcagttatt acttcttg                                                   18
```